United States Patent [19]
Seiffert-Stoeriko et al.

[11] Patent Number: 5,811,539
[45] Date of Patent: Sep. 22, 1998

[54] PROCESS FOR ISOLATING AND PURIFYING NUCLEOTIDE-ACTIVATED SUGARS FROM BIOLOGICAL SOURCES

[75] Inventors: Andreas Seiffert-Stoeriko, Frankfurt; Brigitte Hoersch, Kriftel; Ruediger Marquardt, Frankfurt; Gerhard Kretzschmar, Eschborn; Johannes Meiwes, Idstein, all of Germany

[73] Assignee: Hoechst Aktiengesellschaft, Germany

[21] Appl. No.: 520,690

[22] Filed: Aug. 30, 1995

[30] Foreign Application Priority Data

Sep. 2, 1994 [DE] Germany .......................... 44 31 280.6

[51] Int. Cl.$^6$ ............................. C07H 19/06; C07H 19/16
[52] U.S. Cl. ....................... 536/26.8; 536/17.2; 536/17.9; 536/26.5; 536/28.5; 536/55.3
[58] Field of Search ................................. 536/26.8, 28.5, 536/26.5, 55.3, 17.2, 17.9

[56] References Cited

FOREIGN PATENT DOCUMENTS

| 0 524 143 | 1/1993 | European Pat. Off. . |
|---|---|---|
| 92/22661 | 12/1992 | WIPO . |

OTHER PUBLICATIONS

Comb et al., "The Sialic Acids: Isolation of Cytindine 5'-Monophospho-N-Acetylneuraminic Acid From *Escherichia Coli* K-235", Journal of Biol. Chem., vol. 241, No. 23, (1996) pp. 5637-5642.
Liu et al., "Overproduction of CMP-Sialic Acid Synthetase for Organic Synthesis", J. Am. Chem. Soc., vol. 114, (1992) pp. 3901-3910.
Shoyab et al., "Purification and Properties of the CMP-N-Acetylneuraminic Acid Synthesizing Enzyme From Sheep Brain", Journal of Neurochem., vol. 11, (1964), pp. 639-646.
D, Van Den Eijnden et al., "A Convenient Method for the Preparation of Cytidine 5'-Monophospho-N-Acetylneuraminic Acid,", Hoppe-Seyler's Z. Physiol. Chem. Bd. 353, (1972) pp. 1817-1820.
Auge et al., "An Efficient Synthesis of Cytidine Monophospho-Sialic Acids with Four Immobilized Enzymes", Tetrahedron Letters, vol. 29, No. 7, (1988), pp. 789-790.
Higa et al., "Sialylation of Glycoprotein Oligosaccharides with N-Acetyl-, N-Glycolyl-, and N-o-Diacetylneuraminic Acids", J. Biol. Chem., vol. 260, No. 15, (1985) pp. 8838-8849.
Kittelmann et al., "Preparative Enzymatic Synthesis of Activated Neuraminic Acid by Using a Microbial Enzyme", Annals New York Acad. Sci., vol. 672, (1992), pp. 444-450.
Makino et al., "Chemical Synthesis of Cytidine-5'-Monophosphono-N-Acetylneuraminic Acid (CMP-Neu5Ac)",Tetrahedron Letters, vol. 34, No. 17, (1993), pp. 2775-2778.
Martin et al., Convenient Chemical Synthesis of CMP-N-Acetylneuraminate (CMP-Neu-5-Ac) Tetrahedron Letters, vol. 34, No. 11, (1993) pp. 1765-1768.
Ikeda et al., "Synthesis of Sialic Acid-Containing Nucleotide Sugars: CMP-Sialic Acid Analogs", Carbohydrate Res., vol. 224, (1992), pp. 123-131.
Ichikawa et al., "Efficient Chemical Synthesis of GDP-Fucose", Journal of Org. Chem., vol. 57, (1992), pp. 2943-2946.
Adelhorst et al., "Large-scale Synthesis of B-L-Fucopyranosyl Phosphate and the Preparation GDP-B-L-Fucose", Carbohydrate Res., vol. 242, (1993), pp. 69-76.
Schmidt et al., Stereospecific Synthesis of α-and β-L-Fucopyranosyl Phosphates and of GDP-Fucose via Trichloroachetimidate, Ann. Chem., (1991), pp. 121-124.
Shames et al., "CMP-N-Acetylneuram. Acid. Synth. of Escheri. Coli: Hgh. Lev. Exp., Purif. & Use in Enzym. Synth. CMP-N-Acetylneuram. Acid & CMP-Neuram. Acid Deriv.", Glycobio., vol. 1, No. 2, (1991), pp. 187-191.
Heidlas et al., "Gram-Scale Synthesis of Uridine 5'-Diphospho-N-Acetylglucosamine: Comparison of Enzymatic and Chemical Routes", The Journal of Organic Chemistry, vol. 57, No. 1, (1992), pp. 146-151.
Heidlas et al., "Nucleoside Phosphate Sugars: Syntheses on Practical Scales for Use as Reagents in the Enzymatic Prep. of Oligosaccharides and Glycoconjugates", Acc. Chem Res., vol. 25, (1992), pp. 307-314.
Comb et al., "Isolation of Cytidine-5'-Monophospho-N-Acetylneuraminic Acid", Communications to the Editor, vol. 81, (1959), pp. 5513-5514.
Stiller et al., "Enzymatic Synthesis of B-L-Fucose-1-Phosphate and GDP-Fucose", Ann Chem., (1992) pp. 467-471.
Simon et al., Conv. Synth. of Cytid. 5'-Triphosp., Buanosine 5'-Triphos., & Their Use in Prep. of UDP-Glucose, UDP-Glucuronic Acid, & GDP-Mannose, J. Org. Chem. vol. 55, (1990), pp. 1834-1841.
Wong et al., "Regen. Sugar Nucleo. Enzym. Oligosaccharide Synth.: Use Gal-1-Phosphate Uridlytrans. in the Regen. UDP-Galactose, UDP-2-Deoxygalac., UDP-Galactos.", J. Org. Chem., vol. 57, (1992), pp. 4343-4344.
Pallanca et al., "Chemo-Enzymic Synthesis of Guanosine 5'-Diphosphomannose (GDP-Mannose) and Selected Analogues", Journal Chem. Soc. Perkin Trans. 1, (1993), pp. 3017-3022.
Petrie et al., "A High-Performance Liquid Chromatography Method for the Assay of Cytdine Monophosphate-Sialic Acid Synthetase", Ananlytical Biochem., vol. 131, (1983), pp. 153-159.

*Primary Examiner*—James O. Wilson
*Attorney, Agent, or Firm*—Foley & Lardner

[57] ABSTRACT

The present invention relates to an improved process for isolating and purifying sugar nucleotides, in particular cytidine monophosphate-activated N-acetylneuraminic acid (CMP-Nana), from biological sources. The sugar nucleotides can be obtained from a sugar nucleotide-containing solution, which has been freed of proteins by alcoholic precipitation, by means of an improved column-chromatographic method which uses silica gel as the stationary phase, and at a purity level which requires only a subsequent desalting step to obtain a substantially pure product.

14 Claims, No Drawings

PROCESS FOR ISOLATING AND PURIFYING NUCLEOTIDE-ACTIVATED SUGARS FROM BIOLOGICAL SOURCES

This application takes its priority under 35 U.S.C. §119 from German patent application Serial No. P4431280.6, filed 29 Jun. 1995.

FIELD OF THE INVENTION

The present invention relates to an improved process for isolating and purifying sugar nucleotides, in particular cytidine monophosphate-activated N-acetylneuraminic acid (CMP-Nana), from biological sources.

BACKGROUND OF THE INVENTION

Sugar molecules are present in all cells and are of great importance for life processes. Besides fulfilling a nutritional function, they are also of great importance in providing structural support (cell walls) and as a constituent of nucleic acids. Sugars are present in nature as monomers, oligomers and polymers.

Sugar molecules must first be activated before they can be chemically bonded intracellularly to other molecules or be polymerized. This activation is effected either by the addition of phosphate or by means of derivatization with nucleotides. Both reactions are catalyzed by special enzymes (kinases and glycosyl transferases, respectively) and frequently take place consecutively. In biological cells, the individual sugars are usually linked to a particular nucleoside diphosphate, which brings about the activation. In the case of N-acetylneuraminic acid (Nana), for example, this is cytidine, which, however, is present at the 5'-monophosphate, i.e. as cytidine monophosphate-N-acetylneuraminic acid (CMP-Nana).

Nana is present, together with other sugars, as a polymer constituent (heteropolymer) on the cell surfaces of bacteria (e.g. Neisseriae and Streptococci). In this context, Nana is found in a variety of linkages; for example, in $E.\ coli$, Nana is present as an extracellular homopolymer, colominic acid. In this case, however, it is always the 2,8 and 2,9 linkages that are found (Reglero et al., $Int.\ J.\ Biochem.$ 25:1517 (1993)).

The biosynthesis of these cell wall constituents takes place intracellularly. Nana is first activated by the enzyme CMP-Nana synthase (EC 2.7.7.43), using cytidine triphosphate (CTP), to give CMP-Nana (Kean, $Glycobiol.$, 1:441 (1991)) and then linked into polymer subunits with the aid of sialyl transferases. These polymer subunits are secreted out of the cells using a lipid carrier and are linked together extracellularly into one molecule, the actual polymer (Shockman et al. $Ann.\ Rev.\ Microbiol.$ 37:501 (1983)).

Nana is also found in eukaryotic cells, where, besides being present on the cell wall, it also frequently occurs as the terminal molecule of sugar chains on glycoproteins. These sugar chains are either used for intercellular recognition or are required for maintaining the structure of the proteins.

The importance of oligosaccharides in biological processes is increasingly regarded as representing an opportunity for therapeutic intervention. Thus, it is possible to conceive of pharmaceuticals (e.g. antiinflammatory active compounds) which are based on oligosaccharides (WO 91/19502, WO 92/22661, WO 92/22565 and WO 92/22563, and also Europ. Published Patent Applications 0089 938, 0089 939 and 0089 940). However, a problem in this context is that of preparing adequate quantities of oligosaccharides that are composed of monosaccharides linked together in specific manners. As a consequence of the large number of functional groups, it is possible to conceive of a given oligosaccharide existing in many different isomeric forms, with a variety of possible linkages, only one of which exhibits the desired biological activity. The synthesis of oligosaccharides of the desired configuration solely by chemical means requires the use of protective groups and is laborious and cost-intensive.

A desirable alternative to this would be to use enzymes to prepare these biologically active oligosaccharides. These enzymes (glycosyl transferases) are present ubiquitously in biological material, from which they may be isolated (e.g. Beyer et al., $Adv.\ Enzymol.$ 52:23 (1981)). They exhibit a high degree of specificity with regard to the substrate and the acceptor and consequently with regard to the nature of the chemical linkage, and some of them even allow derivatives to be employed.

When these glycosyl transferases are used, it is necessary for sugar nucleotides to be present as donor substrates. These sugar nucleotides are expensive, chemically labile and difficult to isolate. While total synthesis by chemical means represents an alternative to using enzymes to prepare the sugar nucleotides, it is likewise very laborious and expensive.

One possibility is to isolate the sugar nucleotides directly from biological material. However, these molecules are present at very low concentration within the cell so that it is worthwhile preparing them from this source only in certain cases. The molecules often decompose spontaneously in association with complex preparation steps, resulting in a decrease in the yield.

For this reason, there is a need for an improved, time-saving process for isolating sugar nucleotides directly from biological sources without prior isolation of the enzymes which synthesize sugar nucleotides.

As early as 1959, CMP-Nana was detected in the $E.\ coli$ strain K-235 (ATCC 13027) and isolated from the cells of the strain (Comb et al., $J.\ Am,\ Chem,\ Soc.$ 81:5513 (1959)). To do this, the cells were disrupted by ultrasonication and the CMP-Nana was purified using an anion exchange resin (Dowex-1, $Cl^-$; elution with LiCl). A further paper on the isolation of CMP-Nana (Comb et al., $J.\ Biol.\ Chem.$ 241:5637 (1966)) suggests that, once the cells have been lysed using one of a variety of methods (ultrasonication, French press, etc.) nucleotides and proteins should first be precipitated with ethanol. To do this, the cells are first dried in the presence of acetone, then treated with 80% ethanol, then left to stand at room temperature for 12 hours and finally centrifuged off. The nucleotides in the extract are bound to an ion exchange resin (Dowex-1, $HCO_3$, 200–400 mesh) and eluted at pH 7.4 using triethylammonium hydrogen carbonate. Depending on the quality of the cells, the proportion of CMP-Nana in the total quantity of nucleotide is from 1 to 10%. However, problems occur during the working up. Thus, the ion exchange resin has to be equilibrated with 80% ethanolic buffer for several hours. In addition, the speed of flow of the buffer in the column decreases during the elution (time factor).

Finally, the fractions containing CMP-Nana are combined and further purified by means of paper chromatography or chromatography on SEPHADEX® G-25.

The particular disadvantage of the prior art methods that have been described is that it is possible to prepare only small quantities of CMP-Nana as compared to the potential requirement for this compound. Further, the preparation is elaborate, difficult to reproduce and uneconomical in time.

It is theoretically possible to isolate all the other sugar nucleotides using the above-mentioned methods.

Apart from exploring the possibility of isolating sugar nucleotides from cell extracts, some workers have turned to isolating the enzymes which are required for preparing the activated sugars and then using these enzymes to synthesize the latter. The literature contains many examples of these preparation processes. Examples of nucleotide-activated sugars are UDP-glucose, UDP-galactose, UDP-N-acetylglucosamine, UDP-N-acetylgalactosamine, UDP-glucuronic acid, GDP-fucose, GDP-mannose, dTDP-glucose, dTDP-galactose and CMP-N-acetylneuraminic amid.

A number of studies which deal with the enzymic preparation of CMP-Nana and its purification are cited below. For example, Shames et al. (*Glycobiol.* 1:187 (1991)) used CMP-Nana synthase which was cloned into an *E. coli* overexpression vector to synthesize CMP-Nana, and some of its derivatives, which were isolated by precipitating with ethanol and then drying. Liu et al, (*J. Am. Chem. Soc.*, 114:3901 (1992)) purified CMP-Nana from an enzymic reaction mixture by chromatography on an anion exchange resin (Dowex-1, formate form), in order to separate off the nucleotides, and then by chromatography on a cation exchange rosin (Dowex 50W-X8, $H^+$ form), in order to separate off the excess ammonium bicarbonate. Other authors also prepare CMP-Nana enzymically and purify the product by means of preparative HPLC (Gross et al., *Joint Meeting, Basel*, 366:795 (1985)), by binding to activated charcoal and then eluting with 0.1M $NH_4Cl$ in 50% ethanol (Shoyab et al., *J. Neurochem.*, 11:639 (1964)), by purifying by means of paper chromatography on Whatman 3 MM sheets (van den Eijnden et al., Hoppe-Seyler's *Z. Physiol. Chem.*, 353:1817 (1972)), or by means of silica gel column chromatography (Auge et al., *Tetrahedron Lett.*, 29:789 (1988)). These and other authors purified (CMP-Nana using a propanol:water (7:3) mixture or using an ethanol:ammonium acetate, pH 6.5 (7:3) eluent system (Higa et al.,*J. Biol. Chem.* 260:8838 (1985)), Comparable processes for purifying all the other sugar nucleotides are known and have been reported. Examples of methods which are known for preparing nucleotide-activated sugars are: Kittelmann et al., *Annals New York Acad. Sci.* 672, Enzyme Engineering: 444 (1992); Makino et al. *Tetrahedr, Lett.*, 34:2775 (1993); Martin et al., 34:1765 (1993); Europ. Patent Application 0524 143 Al; Ikeda, *Carbohydr. Res.*, 242:123 (1992); Fean, *Glycobiol.*, 1:441 (1991); Ichikawa et al., *J. Org. Chem.*, 57:2943 (1993); Adelhorst et al., *Carbohydr, Res.*, 242:69 (1993); Schmidt et al., *Lieb. Ann. Chem.*, p. 121, 1991; Stiller et al., *Lieb. Ann. Chem.*, p. 467, 1992; Heidlas et al., *J. Org, Chem.*, 57:146 (1992); Heidlas, *Acc. Chem. Res.*, 25:307 (1992); Simon et al., *J. Org, Chem.*, 55:834 (1990); Wong et al., *Org. Chem.*, 57:4343 (1992); Pallanca et al.,*J. Chem. Soc.* Perkin Trans. 1:3017 (1993).

Owing to the above-mentioned opportunities for exploring the potential for pharmaceuticals based on oligosaccharides, and the possibility of assembling them by means of enzymic glycosylation reactions, there is, therefore, the need for a process for preparing sugar nucleotides of consistent quality in any desired quantity.

SUMMARY OF THE INVENTION

The object of the present invention is to provide an improved process for isolating sugar nucleotides from biological sources (extracts or enzymic mixtures), which process does not suffer from the disadvantages of the prior art methods discussed above.

This object is achieved by a process for isolating and purifying sugar nucleotides from biological sources, in which process a sugar nucleotide-containing solution, which, if necessary, has been freed from insoluble cell constituents, and which can be a cell extract or a reaction solution from an enzymic reaction mixture, is evaporated to dryness (after removing dissolved proteins by means of alcoholic protein precipitation). The resulting, sugar nucleotide-containing residue is taken up in an eluent mixture and chromatographed on silica gel, by a process comprising taking up the sugar nucleotide-containing residue in the eluent mixture. Advantageously, the eluent mixture is comprised of a mixture of a short-chain alcohol and a 0.5 to 1M aqueous solution of an ammonium salt in a ratio by volume of 1:1 to 1:10. The chromatographing is advantageously carried out by (i) mixing the resulting solution with dry silica gel, (ii) loading it, as a viscous mass of honey-like consistency, onto a chromatography column containing commercially available silica gel of arbitrary particle size as the stationary phase, and (iii) eluting the sugar nucleotide under pressure using the said eluent mixture.

The eluent mixture is preferably composed of a mixture of a short-chain alcohol and a 0.5 to 1M aqueous solution of an ammonium salt in a volume ratio of 1:1 to 1:2, in particular in a volume ratio of 1:1.25.

The aqueous solution of the ammonium salt is preferably 1M.

In the eluent mixture, the short-chain alcohol is preferably 2-propanol and the ammonium salt is preferably triethylammonium hydrogen carbonate.

The process of this invention is particularly well suited for isolating and purifying cytidine monophosphate-N-acetylneuraminic acid (CMP-Nana).

However, the process is also suitable for isolating and purifying all the other nucleotide-activated sugars, and their derivatives, from biological sources (cell extracts and enzymic mixtures), in particular for isolating and purifying derivatives of CMP-Nana which were obtained from enzymic mixtures.

Derivatives of N-acetylneuraminic acid which may be mentioned here are: N-acetyl-4-0-acetylneuraminic acid (Neu4,5Ac$_2$), N-acetyl-9-0-acetylneuraminic acid (Neu5, 9Ac$_2$), N-acetyl-7,9-di-O-acetylneuraminic acid (Neu5,7, 9Ac$_3$), N-acetyl-9-0-lactoylneuraminic acid (Neu4Ac9Lt), N-acetyl-4-0-acetyl-9-0-lactoylneura3minicacid (Neu4, 5Ac$_2$9Lt), N-acetylneuraminic acid-9-phosphate (Neu5Ac9P), N-glycolylneuraminic acid (Neu5Gc), N-glycolyl-9-0-acetylnduraminic acid Neu9Ac5Gc), N-glycolyl-9-0-lactoylneuraminic acid (Neu5Gc9Lt), N-glycolylneuraminic acid-8-sulfate (NeuSGcSS). The following may also be added to this list: 5-azidoneuraminic acid, N-acetyl-9-azido-9-deoxyneuraminic acid, N-acetyl-9-acetamido-9-deoxyneuraminic acid, carbomethoxy-N-acetylneuraminic acid and carbobenzyloxy-N-acetylneuraminic acid.

DETAILED DESCRIPTION OF THE INVENTION

The process according to the present invention is described in detail below, proceeding from a sugar nucleotide-containing solution (cell extract or enzymic mixture).

The sugar nucleotide-containing solution is mixed with alcohol, for example ethanol or propanol, up to a final concentration of from 40 to 60%, in particular approximately 50% (vol./vol.), and this mixture is incubated at 4° C. for 1 hour. The precipitated proteins, and also the insoluble cell constituents and, if used, the glass beads, are separated off in a suitable manner and the supernatant which remains is concentrated in vacuo (subjected to rotary evaporation or lyophilized).

The supernatant, which has been concentrated to dryness, is dissolved in the elution solvent (for the subsequent silica gel column chromatography) and this solution is mixed with dry silica gel so that a viscous mass of honey-like consistency is formed. A mixture of short-chain alcohols and aqueous solution of ammonium salts (e.g., 0.5 to 1M), advantageously in a volume ratio of 1:1 to 1:10, preferably 1:1 to 1:2, is suitable for use as the eluent. A mixture of, for example, 2-propanol and a 1M aqueous solution of triethylammonium hydrogen carbonate, in a volume ratio of 1:1.25, is particularly suitable for use as the eluent. Commercially obtainable silica gels of arbitrary particle sizes may be employed for the separation. The mixture which has been loaded on is eluted under pressure.

The collected fractions are examined by means of suitable detection methods, preferably by means of thin layer chromatography (TLC) or by means of HPLC, The TLC can be carried out on a suitable support (e.g. silica gel 60 HPTLC plates or the like). The above-mentioned eluent represents a suitable eluent for this purpose. The detection methods which are customarily described in the literature may suitably be used in the HPLC analysis (e.g. Petrie et al., *Anal. Biochem.* 131:153 (1983)).

As a rule, the silica gel column chromatography gives rise to sugar nucleotide-containing fractions which are of differing purity and which, depending on the extent of contamination, either have to be purified further by anion exchange chromatography (lower purity) or else simply have to be desalted by means of gel filtration (highly pure). All the fractions which contain the desired product are pooled (in accordance with the extent to which they are contaminated) and are concentrated in vacuo.

Those fractions which have to be purified further by means of anion exchange chromatography are dissolved in a suitable eluent mixture, generally, the running buffer of the column. The subsequent chromatography procedes using the elution buffer specified by the supplier, in each case depending on the nature of the anion exchange material employed. Positive fractions are detected by the above-mentioned detection methods, concentrated in vacuo and then further desalted and purified by means of gel filtration.

Fractions that do not have to be purified by anion exchange chromatography can be further purified and/or desalted directly by means of gel filtration (e.g. BIOGEL® P2 or SEPHADEX® G 10 to G 200). Under these circumstances, the product elutes as the triethylammonium hydrogen carbonate salt. Positive fractions are identified by means of the specified detection methods, concentrated in vacuo and stored at −20° C.

The sugar nucleotides that have been purified in this manner exhibit signals in NMR spectroscopy that are identical to the spectra given in the literature for authentic sugar nucleotides.

The products are found to be active in biological tests, i.e. when the sugar is transferred by means of an appropriate glycosyl transferase.

The following examples serve to illustrate the invention and are not intended to restrict the latter in any way.

EXAMPLE 1

The process of this invention for isolating and purifying nucleotide activated sugars will be explained in more detail using the isolation of cytidine monophosphate-N-acetylneuraminic acid (CMP-Nana) from *E. coli* Z3626 as an example. This latter bacterial strain is known from the literature (Steenbergen et al., *J. Bacteriol.* 174:1099 (1992)). It possesses a mutation in the sialyl transferase which polymerizes the CMP-Nana which is formed intracellularly. As a consequence of this defect, CMP-Nana accumulates intracellularly. a) Culture and fermentation of the *E. coli* Z3626 strain The strain grows in a medium as is described in (Uchida et al., *Agr. Biol. Chem.*, 37:2105 (1973)). The composition of this medium was further optimized with a view to obtaining a high intracellular concentration of CMP-Nana, as follows.

Optimization of the carbon source:

A variety of carbon sources were tested (lactose, saccharose, maltose, glucose, galactose, sorbitol, mannost and glycerol). This data indicated that glucose was the most suitable substrate.

Optimizing the glucose concentration:

The optimum concentration of glucose for forming CMP-Nana was found to be 30 g/l.

Optimizing the nitrogen source:

Both complex and defined nitrogen sources were used for these optimization experiments. It was found that yeast extract gave the best yield.

Optimizing the yeast extract concentration:

The optimum concentration for forming CMP-Nana was found to be 2 g/l.

Optimizing the culture:

The strain exhibits the highest intracellular concentrations of CMP-Nana when cultivated at a temperature of 30° to 40° C. for 16 to 24 hours, at a pH of 6 to 8, while being well aerated.

Intracellular concentration of CMP-Nana under the optimized conditions:

The strain forms approximately 150 mg of CMP-Nana per 10 l of culture.

EXAMPLE 2

Isolation and disruption of the cells

The culture is terminated as soon as the cell density has reached an appropriate value, i.e. after about 11 to 30 hours. The cells are harvested by centrifugation and washed with a buffer solution such as, for example, 10 to 100 mM Tris/HCl, pH 6 to 8. The sedimented cells are resuspended in a suitable buffer (see above) and in the additional presence of 1 to 10 mM EDTA and 0.1 to 1 mM NaF) and then disrupted in the cold by standard methods such as, for example, by shaking with fine glass beads, by ultrasonication or by using a French press. To facilitate the disruption, lysozyme (1 to 10 mg/ml) may be used as well. This mixture is used as the source of CMP-Nana (crude extract).

The proteins are then precipitated by adding ethanol up to a final concentration of 50%. After the mixture has been incubated at 4° C. for 1 hour, it is centrifuged and the supernatant is concentrated in vacuo (subjected to rotary evaporation or lyophilized).

EXAMPLE 3

Purification of CMP-Nana by means of silica gel column chromatography

The supernatant that has been concentrated to dryness as in Example 2 is dissolved in a small amount of isopropanol: 1M triethylammonium hydrogen carbonate in a ratio by volume of 1:1.25 (eluent for the silica gel column), and this solution is mixed with dry silica gel to form a mass of a honey-like consistency. This mixture is loaded onto a silica gel column and eluted under pressure using the eluent, and the fractions are collected. The use of triethylammonium hydrogen carbonate buffer is important as this ensures that the product can be isolated in the salt form in which it is most stable.

The fractions are examined using suitable detection methods, preferably using TLC or using HPLC, The TLC can be carried out on a suitable support (e.g. silica gel 60 HPTLC plates (Merck) or the like). A suitable eluent for this purpose has the composition isopropanol:1M ammonium acetate 2.4:2.

The measurement methods which are customarily cited in the literature are suitable for use when carrying out the analysis by means of HPLC (e.g. Petrie et al., *Anal. Biochem.*, 131:153 (1983)).

Generally, the silica gel column chromatography procedure results in the production of fractions of differing levels of purity that, depending on the extent to which they are contaminated, have either to be further purified, e.g., by anion exchange chromatography, or have simply to be desalted by means of gel filtration (e.g. Biogel P2 200 to 400 mesh (Biorad) or Sephadex G-10 (Pharmacia)) to be suitable for use.

All the positive fractions are combined in accordance with the extent to which they are contaminated and are concentrated in vacuo.

Those fractions that are to be further purified by anion exchange chromatography are dissolved in the eluent for anion exchange chromatography and loaded onto the column. For this purpose, anion exchange chromatography using Dowex resin is preferable.

Fractions that need not be purified by anion exchange chromatography can be further purified and/or desalted by means of gel filtration (preferably using Biogel P2). The product elutes as the triethylammonium hydrogen carbonate salt.

Positive fractions are identified using the above-mentioned detection methods, lyophilized and frozen at −20° C.

The samples which had been purified in this manner were examined by $^1$H NMR spectroscopy to determine whether they were of the correct structure and whether any impurities were present which were not detectable with the said measurement methods. The spectra obtained were compared with those in the literature.

EXAMPLE 4

Examination of the product by 1H-NMR spectroscopy (Liu et al., *J. Am. Chem. Soc.* 114:3901 (1992)) H-NMR: (300 MHz, $D^2O$): δ 1.66 (1 H, ddd, J=13, 12 Hz, H-3ax), 2.05 (3 H, s, NAc), 2.5 (1 H, dd, J=13, 4.8 Hz, H-3eq), 3.46 (1 H, d, J=9.6 Hz, H - 7), 3.63 (1 H, dd, J=6.6, 12 Hz, H-9a), 3.9 (1 H, dd, J=12, 2.4 Hz, H-9b), 3.94 to 4.0 (2 H, m, H-8, H-5) 4.06 (1 H, ddd, 10=10, 5, 12 Hz, H-5), 4.15 (1 H, dd, J=10, 1.5 Hz, H-6), 4.22–4.28 (3 H, m, H-4', H-51), 4.29–4.38 (2 H, m, H-31' H-2') 6.00 (1 H, d, i=5 Hz, H-1'), 6.13 (1 H, d, J=7.8 Hz, H-5"), 7.98 (1 H, d, J=7.6 Hz, H-6")

EXAMPLE 5

Enzymic synthesis of α-D-Neu5Ac-(2,6)-β-D-Gal-(1,4)-β-D-GlcNAc-O $(CH_2)_6NH_2$

The resulting product is of a purity such that it can be employed for, and is active in, enzymic reactions (sialyl transferase reactions), 12 mg (25 μmol) of β-D-Gal- (1,4) -β-D-GlcNAc-O $(CH_2)_6$ $NH_2$ are dissolved in 2 ml of 0.05M cacodylate buffer, and 15.4 mg (25 μmol) of CMP-neuraminic acid, prepared in accordance with Example 2, 1.5 mg of bovine serum albumin and 2 mg $MnCl_2$ are added to this solution. After the pH of the mixture has been adjusted to 7.4, 40 mU of α-2,6-sialyl transferase (from rat liver, Boehringer Mannheim) and 20 U of alkaline phosphatase (from calf intestine, Boehringer Mannheim) are added and the mixture is then incubated at room temperature for 10 days. For the working up, chromatography is carried out on Biogel P2 (Biorad) using water as the eluent. The trisaccharide is obtained after freeze drying. Yield: 11 mg α-D-Neu5Ac-(2, 6)-β-D-Gal-(1,4)-β-D-GlcNAc-O $(CH_2)$ , $NH_2$.

$^1$H-NMR (300 MHz, $D_2O$): δ 1.35 to 1.42 (4 H, m, CH2-spacer), 1.54 to 1.7 (4 H, m, CH2-spacer); 1.72 (1 H, dd, H-3ax), 2.04 (3 H, s, $NAc_{Neu5Ac}$), 2.06 (3H, s, $NAc_{GlcNAc}$), 2,68 (1 H, dd, H-3eq), 3.0 (2 H, t, $CH_2$-spacer), 3.5 to 4.0 (21 H, m), 4.46 (1 H, d, H-1-Gal), 4.56 (1 H, d, H-1-GlcNAc)

$^{13}$C-NMR (300 MHz, $D_2O$): δ 22.35 ($CH_3$-Neu5Ac), 22.63 ($CH_3$-GlcNAc), 24.93, 25.54, 26.97, 28.65 (spacer-$CH_2$), 39,72 ($CH_2-NH_2$),, 40,40 (C3"), 52.18 (C5"), 55.20 (C2), 60.71 (C6), 62.97 (C9"), 63.67 (C6'), 68.53 (C7"), 6872 (C4', C4"), 70.64 ($CH_2$-O), 71.03 (C2'), 72.0 (C8"), 72.77 (C3, C3'), 72.85 7(C6"), 74.0 (C5'), 74.78 (C5), 81.1 (C4), 100.8 (C2"), 101 (C1), 104 (C1') 173.5 (C1"), 174.5 (Ac-GlcNAc), 175 (Ac-Nei5Ac)

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A process for isolating and purifying an N-acetyl neuraminic acid or derivative sugar nucleotide of N-acetyl neuraminic acid from a biological source comprising a Protein-containing cell extract or enzymic reaction mixture, comprising the steps of:

(A) removing any dissolved proteins present in said biological source by means of alcoholic protein precipitation to yield a first solution, said first solution comprising a sugar nucleotide;

(B) evaporating said first solution to dryness to yield a sugar nucleotide-containing residue;

(C) dissolving said sugar nucleotide-containing residue in an eluent mixture comprising a short-chain alcohol and an aqueous solution of an ammonium salt, thereby forming a second solution;

(D) mixing said second solution with dry silica gel to form a viscous mass;

(E) transferring said viscous mass to a chromatography column containing silica gel as the stationary phase; and (F) chromatographing the contents of said viscous mass to yield a sugar nucleotide.

2. The process as claimed in claim 1, wherein the concentration of said ammonium salt in said aqueous solution is 0.5–1.0M.

3. The process as claimed in claim 2, wherein said short-chain alcohol and said aqueous solution of an ammonium salt are present in said eluent mixture in a ratio by volume of from about 1:1 to about 1:10.

4. The process as claimed in claim 2, wherein the ratio by volume of said short-chain alcohol to said 0.5 to 1.0M aqueous solution of said ammonium salt is 1:1 to 1:2.

5. The process as claimed in claim 2, wherein the ratio by volume of said alcohol to said solution of said ammonium salt is 1:1.25.

6. The process as claimed in claim 1, wherein said short-chain alcohol is 2-propanol.

7. The process as claimed in claim 3, wherein said short-chain alcohol is 2-propanol.

8. The process as claimed in claim 1, wherein said ammonium salt is triethylammonium hydrogen carbonate.

9. The process as claimed in claim 3, wherein said ammonium salt is triethylammonium hydrogen carbonate.

10. The process as claimed in claim 1, wherein said chromatographing comprises eluting said sugar nucleotide from said stationary phase under pressure using said eluent mixture.

11. The process as claimed in claim 1, wherein:

said short-chain alcohol and said aqueous solution of said ammonium salt are present in said eluent mixture in a ratio by volume of 1:1 to 1:2;

the concentration of said aqueous solution of said ammonium salt is 1M;

said short-chain alcohol is 2-propanol;

said ammonium salt is triethylammonium hydrogen carbonate; and said sugar nucleotide is cytidine monophosphate-N-acetylneuraminic acid.

12. The process as claimed in claim 1, wherein said biological source comprises a cell extract or a reaction solution from an enzymic reaction mixture.

13. The process as claimed in claim 12, wherein Step (A) is preceded by the step of freeing said cell extract or reaction solution from insoluble constituents.

14. The process according to claim 1 wherein said N-acylneuraminic acid or derivative thereof sugar nucleotide is cytidine monophosphate N-acetyl-neuraminic acid.

* * * * *